United States Patent
Pannala et al.

(10) Patent No.: US 11,020,719 B2
(45) Date of Patent: Jun. 1, 2021

(54) METHOD AND REACTOR FOR PYROLYSIS CONVERSION OF HYDROCARBON GASES

(71) Applicant: SABIC Global Technologies B.V., Bergen op Zoom (NL)

(72) Inventors: Sreekanth Pannala, Sugar Land, TX (US); Vladimir Shtern, Houston, TX (US); Lei Chen, Sugar Land, TX (US); David West, Bellaire, TX (US)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 16/977,644

(22) PCT Filed: Mar. 7, 2019

(86) PCT No.: PCT/US2019/021114
§ 371 (c)(1),
(2) Date: Sep. 2, 2020

(87) PCT Pub. No.: WO2019/173570
PCT Pub. Date: Sep. 12, 2019

(65) Prior Publication Data
US 2021/0046440 A1     Feb. 18, 2021

Related U.S. Application Data

(60) Provisional application No. 62/639,577, filed on Mar. 7, 2018.

(51) Int. Cl.
*C07C 2/78* (2006.01)
*B01J 12/00* (2006.01)
(Continued)

(52) U.S. Cl.
CPC .............. *B01J 6/008* (2013.01); *B01J 4/005* (2013.01); *B01J 12/005* (2013.01);
(Continued)

(58) Field of Classification Search
CPC .............. C07C 11/24; C07C 2/78; B01J 6/008
See application file for complete search history.

(56) References Cited

U.S. PATENT DOCUMENTS

| 4,421,476 A | 12/1983 | Gulden et al. |
| 4,724,272 A * | 2/1988 | Raniere .................... C10G 9/38 |
| | | 585/500 |

(Continued)

FOREIGN PATENT DOCUMENTS

| CN | 1503732 A | 6/2004 |
| CN | 101249949 A | 8/2008 |

(Continued)

OTHER PUBLICATIONS

AMC Pamphlet, AMCP 706-285. Engineering Design Handbook: Elements of Aircraft and Missile Propulsion. Chapter 4: Compressible Flow in Nozzles, pp. 4-1 to 4-42. Headquarters, U.S. Army Materiel Command. Jul. 1969. (Year: 1969).*

(Continued)

*Primary Examiner* — Jennifer A Leung
(74) *Attorney, Agent, or Firm* — Grady K. Bergen; Paul I. Herman; Griggs Bergen LLP

(57) ABSTRACT

A pyrolysis reactor (12) and method for the pyrolysis of hydrocarbon gases (e.g., methane) utilizes a pyrolysis reactor (12) having a unique burner assembly (44) and pyrolysis feed assembly (56) that creates an inwardly spiraling fluid flow pattern of the feed gases to form a swirling gas mixture that passes through a burner conduit (46) with a constricted neck portion or nozzle (52). At least a portion of the swirling gas mixture forms a thin, annular mixed gas flow layer immediately adjacent to the burner conduit (46). A portion of the swirling gas mixture is combusted as the swirling gas mixture passes through the burner conduit (46) and a portion of combustion products circulates in the burner assembly (Continued)

(44). This provides conditions suitable for pyrolysis of hydrocarbons or light alkane gas, such as methane or natural gas.

14 Claims, 12 Drawing Sheets

(51) Int. Cl.

| | | |
|---|---|---|
| *B01J 19/24* | (2006.01) | |
| *B01J 6/00* | (2006.01) | |
| *B01J 4/00* | (2006.01) | |
| *B01J 19/00* | (2006.01) | |
| *B01J 19/02* | (2006.01) | |
| *C07C 11/24* | (2006.01) | |

(52) U.S. Cl.
CPC .......... *B01J 19/0053* (2013.01); *B01J 19/02* (2013.01); *B01J 19/2405* (2013.01); *B01J 19/246* (2013.01); *B01J 19/2415* (2013.01); *C07C 2/78* (2013.01); *B01J 2204/002* (2013.01); *B01J 2219/00094* (2013.01); *B01J 2219/1943* (2013.01); *C07C 11/24* (2013.01)

(56) References Cited

U.S. PATENT DOCUMENTS

| | | | |
|---|---|---|---|
| 5,789,644 | A | 8/1998 | Passler et al. |
| 5,886,056 | A | 3/1999 | Hershkowitz et al. |
| 6,365,792 | B1 | 4/2002 | Stapf et al. |
| 6,799,427 | B2 | 10/2004 | Calvez et al. |
| 7,956,228 | B2 | 6/2011 | Bartenbach et al. |
| 8,080,697 | B2 | 12/2011 | Lin et al. |
| 8,801,814 | B2 | 8/2014 | Grossschmidt et al. |
| 9,718,963 | B2 | 8/2017 | Rodriguez et al. |
| 10,407,305 | B2 * | 9/2019 | Kern ................. B01J 19/24 |
| 2002/0064741 | A1 | 5/2002 | Bartenbach et al. |
| 2005/0065391 | A1 | 3/2005 | Gattis et al. |
| 2010/0126176 | A1 * | 5/2010 | Kim .......................... F23R 3/14 60/748 |
| 2011/0054231 | A1 | 3/2011 | Peterson |
| 2012/0048713 | A1 | 3/2012 | Yeung |
| 2013/0039840 | A1 | 2/2013 | Rodriguez et al. |
| 2014/0058178 | A1 * | 2/2014 | Bedard ................. B01J 19/02 585/539 |
| 2015/0165414 | A1 * | 6/2015 | Gattupalli ................ C07C 2/78 585/536 |

FOREIGN PATENT DOCUMENTS

| | | | |
|---|---|---|---|
| CN | 101525118 | A | 9/2009 |
| CN | 101063039 | A | 3/2011 |
| CN | 102875837 | A | 1/2013 |
| CN | 107001185 | A | 8/2017 |
| GB | 821856 | | 10/1959 |
| GB | 921305 | | 3/1963 |
| GB | 958046 | | 5/1964 |
| GB | 1320631 | A * | 6/1973 ............. F23D 14/00 |
| WO | WO2014027985 | A1 | 2/2014 |
| WO | WO2014031462 | A1 | 2/2014 |
| WO | WO2015028539 | A1 | 3/2015 |
| WO | WO2015088614 | A1 | 6/2015 |
| WO | WO2016209648 | A1 | 12/2016 |
| WO | WO2017205067 | A1 | 11/2017 |

OTHER PUBLICATIONS

International Search Report and Written Opinion of the International Search Authority (ISA/US) dated May 17, 2019 in unterpart International PCT Patent Application No. PCT/US2019/021114.

Chinese Office Action dated Jan. 25, 2021 in counterpart Chinese Patent Application No. 201980017611.8.

Extended European Search Report dated Feb. 22, 2021 in counterpart European Application No. 19765124.3.

* cited by examiner

METHOD AND REACTOR FOR PYROLYSIS CONVERSION OF HYDROCARBON GASES

CROSS-REFERENCE TO RELATED APPLICATIONS

This application is a national stage application under 35 U.S.C. § 371 of International PCT Application No. PCT/US2019/021114, filed Mar. 7, 2019, which claims the benefit of U.S. Provisional Application No. 62/639,577, filed Mar. 7, 2018, each of which is incorporated herein by reference in its entirety.

TECHNICAL FIELD

The invention relates to conversion methods for hydrocarbons, particularly alkanes, to pyrolysis products and the reactor design for such conversion.

BACKGROUND

The traditional methods of converting lower molecular weight carbon-containing molecules to higher molecular weights are numerous. The most prevalent methods involve oxidative coupling, partial oxidation, or pyrolysis. Each method has its own benefits and its own challenges. High temperature pyrolysis of methane has commonly been used for production of acetylene commercially. Depending on the method used to supply the necessary endothermic heat of pyrolysis, the methane and/or hydrocarbon pyrolysis to acetylene is broadly categorized into single-stage or two-stage processes.

The single-stage method produces acetylene mainly through partial oxidation of methane. A representative single-stage process is that developed by BASF, which is described in U.S. Pat. No. 5,789,644. This process has been commercialized at a 50 KTA scale using multiple reactors in Germany and the U.S. In this process, natural gas serves for the hydrocarbon feed and pure oxygen serves as the oxidant. The two streams are premixed in a diffuser, and the premixed fuel rich gas is burnt using a burner block through partial oxidation. This process usually operates at atmospheric pressure or slightly elevated pressure, with the volume ratio of oxygen to natural gas at about 0.6. A major disadvantage of such a design is the flashback risks of the premixed flame under various feedstock and operating conditions, as well as the plurality of burners used, which increases the probability of failure or shutdown of the reactor and also increases the cost of building the reactor.

In two-stage acetylene production, the processes convert methane to acetylene through pyrolysis, using the thermal energy of the high temperature product gases from complete combustion. Those processes described in British Patent Nos. GB921,305 and GB958,046, U.S. Pat. App. Pub. No. US2005/0065391, and SABIC's U.S. Pat. No. 8,080,697 are representative technologies for such two-stage process. This process comprises two main reaction zones followed by a quenching zone. The first reaction zone serves as a near stoichiometric combustor to supply the necessary endothermic heat of hydrocarbon pyrolysis taking place in the second reaction zone, into which a fresh hydrocarbon feed such as methane is introduced. In the quenching zone, water or heavy oil is used as a coolant to cool down instantaneously the hot product gas from the pyrolysis zone. A major disadvantage of such a design is large heat losses that are incurred in cooling the combustor walls in order to protect them.

The proposed invention is free from the above-discussed disadvantages of conventional single- and two-stage processes. It provides a simple, safe, and efficient process of nearly simultaneous mixing, combustion, and pyrolysis. The process is realized by the proposed special design including a converging-diverging burner nozzle and disk-like inlets for nearly tangential injection of both hydrocarbon and oxidizer gases.

These improvements are described in more detail next.

SUMMARY

A pyrolysis reactor for the pyrolysis of hydrocarbon gases has a pyrolysis reactor vessel having a reactor wall that defines a pyrolysis reaction chamber. A burner assembly of the reactor has a burner conduit with a circumferential wall that surrounds a central longitudinal axis and extends from opposite upstream and downstream ends of the burner conduit. The circumferential wall tapers in width from the downstream and upstream ends to an annular constricted neck portion located between the downstream and upstream ends of the burner conduit. The downstream end of the burner conduit is in fluid communication with the reaction chamber of the pyrolysis reactor, with the upstream end of the burner conduit forming a burner assembly inlet.

The pyrolysis reactor further includes a pyrolysis feed assembly in fluid communication with the burner assembly inlet, with the central axis passing through the pyrolysis feed assembly. The feed assembly has a downstream feed assembly wall that extends circumferentially around and joins the upstream end of the burner assembly inlet. The downstream feed assembly wall is oriented perpendicular to the central axis. An upstream feed assembly wall is axially spaced upstream from the downstream wall along the central axis and extends perpendicularly across the central axis. A gas partition wall of the feed assembly is axially spaced between the downstream and upstream feed assembly walls and is oriented perpendicular to the central axis and has a central opening that surrounds the central axis of the burner conduit. The partition wall defines an annular hydrocarbon gas inlet flow space between the downstream feed assembly wall and the partition wall and an annular oxygen gas inlet flow space between the partition wall and the upstream feed assembly wall so that hydrocarbon gas feed and oxygen gas feed are introduced and passed through said flow spaces perpendicularly to the central axis of the burner conduit in an inwardly spiraling fluid flow pattern within said flow spaces about the central axis of the burner conduit.

The area extending from the central opening of the partition wall to the burner assembly inlet defining a mixing chamber of the pyrolysis feed assembly. Oxygen gas feed from the oxygen gas inlet flow space and hydrocarbon gas feed from the hydrocarbon gas inlet flow space is discharged into the mixing chamber so that the oxygen and hydrocarbon feed gases are mixed together and form a swirling gas mixture within the mixing chamber, the swirling gas mixture passing through the burner conduit.

In particular embodiments, at least one of the annular hydrocarbon gas and oxygen gas inlet flow spaces is provided with circumferentially spaced apart guide vanes oriented to facilitate the spiraling fluid flow within said at least one of the inlet flow spaces. In certain applications, the guide vanes are movable to selected positions to provided selected azimuthal-to-radial velocity ratios of each of the light alkane gas feed stream and the oxygen gas feed stream within the annular inlet flow spaces.

In many embodiments, the reactor wall is cylindrical. In certain instances, the circumferential wall of the burner conduit from the downstream end to the annular constricted neck portion, and optionally an upstream portion of the reactor wall of the pyrolysis reaction chamber that joins the circumferential wall of the burner conduit, is configured as a smooth, continuous wall that follows contour lines of an ellipsoidal cap or spherical cap shape. The interior of the reactor wall may be a refractory material in some embodiments.

In a method of converting light alkanes to pyrolysis products, a pyrolysis feed is introduced into a pyrolysis reactor. The pyrolysis reactor vessel has a reactor wall that defines a pyrolysis reaction chamber. The reactor further includes a burner assembly having a burner conduit with a circumferential wall that surrounds a central longitudinal axis and extends from opposite upstream and downstream ends of the burner conduit. The circumferential wall has an annular constricted neck portion located between the downstream and upstream ends of the burner conduit. The downstream end of the burner conduit is in fluid communication with the reaction chamber of the pyrolysis reactor, the upstream end of the burner conduit forming a burner assembly inlet.

In the method, the reactor further includes a pyrolysis feed assembly having an annular alkane gas flow space and an annular oxygen gas flow space that discharge into a central mixing chamber that is in fluid communication with the burner assembly inlet. An alkane-containing gas feed stream of the pyrolysis feed is introduced into the annular alkane gas flow space and an oxygen-containing gas feed stream of the pyrolysis feed is introduced into the annular oxygen gas flow space. The gases are introduced so that the alkane-containing gas feed stream and the oxygen-containing gas feed stream pass through said flow spaces perpendicularly to the central axis of the burner conduit in an inwardly spiraling fluid flow pattern within said flow spaces that flows about the central axis of the burner conduit, with the oxygen-containing gas feed stream from the oxygen gas flow space and alkane-containing gas feed stream from the alkane gas flow space being discharged into the mixing chamber so that the alkane-containing gas and oxygen-containing gas feed streams are mixed together and form a swirling gas mixture within the mixing chamber. The swirling gas mixture is allowed to pass through the burner conduit, with at least a portion of the swirling gas mixture forming a thin, annular mixed gas flow layer immediately adjacent to the burner conduit, and wherein a portion of the swirling gas mixture is combusted as the swirling gas mixture passes through the burner conduit to provide conditions suitable for pyrolysis of the light alkane gas from the alkane-containing gas feed stream within the pyrolysis reaction chamber of the reactor vessel. A portion of the light alkane gas is converted to pyrolysis products within the pyrolysis reaction chamber. The pyrolysis products are removed from the reaction chamber of the reactor vessel.

In particular embodiments, a back flow of flue gases is formed within the pyrolysis reactor that flows upstream and radially inward from the thin, annular mixed gas flow layer along the central longitudinal axis toward the upstream end of the burner conduit.

In certain applications, the light alkane gas is a methane gas or natural gas. The methane gas or natural gas (NG) feed and the oxygen gas feed may be introduced into the pyrolysis feed assembly in a $CH_4/O_2$ or $NG/O_2$ molar ratio of from 1 to 5.

Pyrolysis products may be removed from the reaction chamber and be quenched within a quenching unit.

The azimuthal-to-radial velocity ratio of each of the light alkane gas feed stream and the oxygen gas feed stream within the annular flow spaces may be from 0 to 30.

The light alkane gas feed stream and the oxygen gas feed stream are each introduced into the respective annular flow spaces in the same rotational direction.

At least one of the annular hydrocarbon gas and oxygen gas flow spaces is provided with circumferentially spaced apart guide vanes oriented to facilitate the rotating swirling fluid flow within said at least one flow spaces. In certain embodiments, the guide vanes may be movable to selected positions to provided selected azimuthal-to-radial velocity ratios of each of the light alkane gas feed stream and the oxygen gas feed stream within the annular flow spaces.

The reactor wall may be cylindrical. And the circumferential wall of the burner conduit from the downstream end to the annular constricted neck portion, and optionally an upstream portion of the reactor wall of the pyrolysis reaction chamber that joins the circumferential wall of the burner conduit, may be configured as a smooth, continuous wall that follows contour lines of an ellipsoidal cap or spherical cap shape. The interior of the reactor wall may be a refractory material.

The annular alkane gas flow space and the annular oxygen gas flow space may be defined by planar walls of the pyrolysis feed assembly that are oriented perpendicular to the central axis of the burner conduit. The annular alkane gas flow space may be located at a position along the central axis downstream from the annular oxygen gas flow space.

BRIEF DESCRIPTION OF THE DRAWINGS

For a more complete understanding of the embodiments described herein, and the advantages thereof, reference is now made to the following descriptions taken in conjunction with the accompanying figures, in which.

DETAILED DESCRIPTION

In the present disclosure, a novel system is utilized that transforms a two-stage combustion-pyrolysis process into a single stage. The system and process utilizes a "combustion and pyrolysis while mixing" concept. This is achieved by utilizing annular highly swirled jets of feed gas and oxygen gas under particular fluid-dynamics that are fed to a unique burner assembly of a pyrolysis reactor. Different from the conventional single-stage partial oxidation methods that utilize a premixed flame, the combustion in the present reactor design features a compact flame with complete combustion from nearly non-premixed gases [i.e., the gases start to mix as they meet within a mixing chamber of a feed assembly of the reactor] that provide high gas temperatures of up to about 2800° C. The combustion reaction supplies the necessary heat for pyrolysis of excess methane gas or other feed gas that is entrained into the hot combustion gases through the direct contact and recirculation in the same reaction chamber of the pyrolysis reactor.

It should be noted that throughout the description, although the discussion and examples presented may relate to the conversion of methane to acetylene and other pyrolysis products, the methods and systems presented may be equally applicable to the conversion of other non-methane alkane compounds to higher value alkyne compounds or to other hydrocarbons, which may be non-alkane hydrocarbons, into pyrolysis products.

Figure 1:
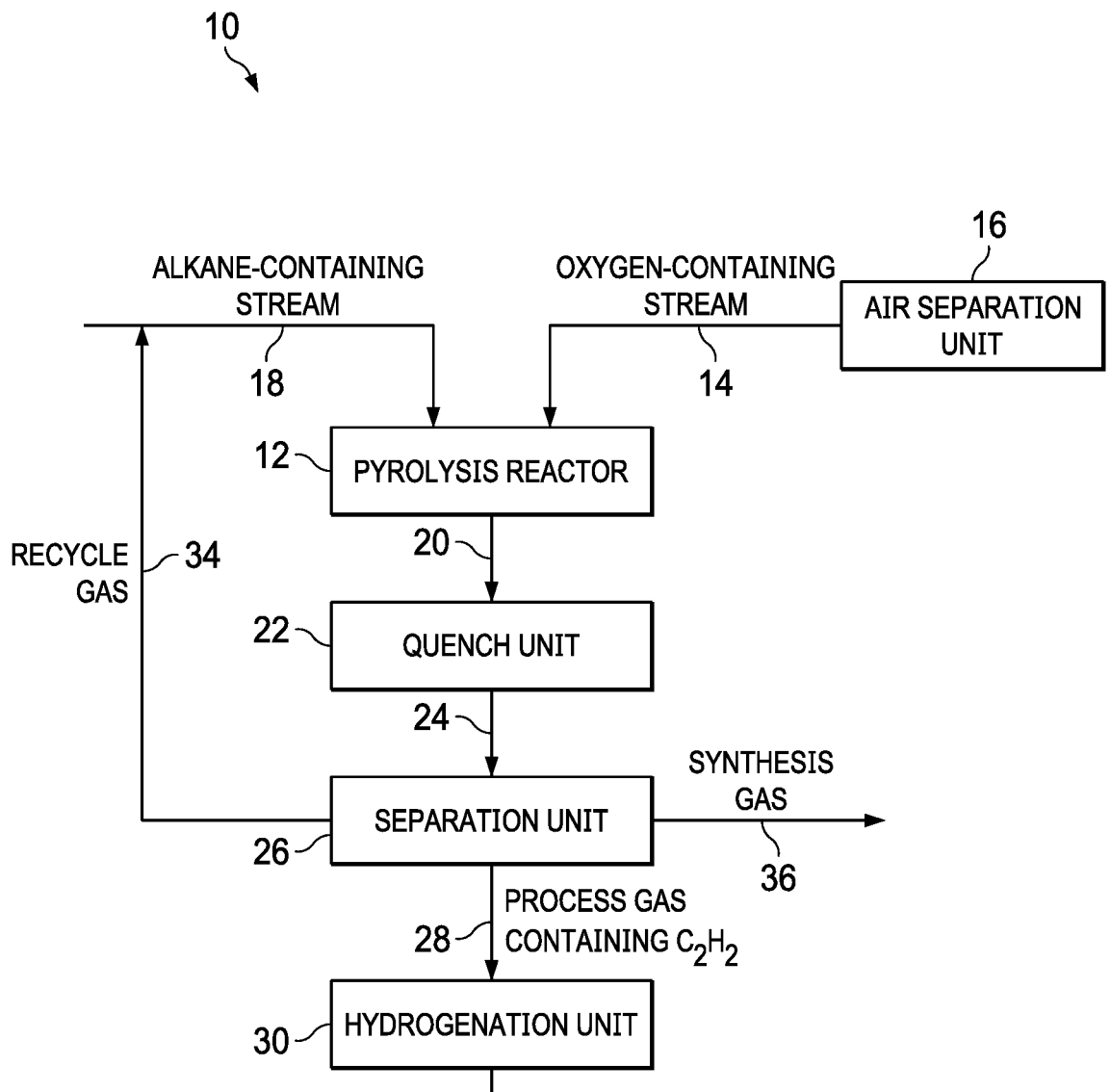
FIG. 1 is a process flow diagram of a pyrolysis system for converting hydrocarbon gases, such as methane, into pyrolysis products in accordance with particular embodiments.

Referring to FIG. 1, a pyrolysis system 10 for the pyrolysis of methane or other hydrocarbons is shown. The system 10 includes a pyrolysis reactor 12, which is described in more detail later on. An oxygen-containing gas feed stream 14 is fed to the reactor 12. The oxygen-containing gas feed 14 may be a concentrated oxygen-gas feed, wherein a majority of the feed (i.e., >50 mol %) is composed of oxygen gas ($O_2$). In many instances, the oxygen-containing gas will be a high-purity oxygen-containing gas feed composed of $O_2$ in an amount of from 20 mol % to 100 mol % of the oxygen gas feed stream. This may be that provided from an air separation unit (ASU) 16 used for separating oxygen gas from air or other oxygen-gas source. Air may also be used as the oxygen-containing gas. In cases where air is used as the oxygen-containing gas, or cases where there are large amounts of impurities (e.g., $N_2$) in the oxygen-containing gas feed, separation of such impurities from the product may be necessary downstream.

A hydrocarbon-containing gas feed stream 18 is fed to the reactor 12 separately from the oxygen gas feed stream 14. The feed stream 18 may be a hydrocarbon gas that contains one or more alkanes. These may be light alkanes such as $C_1$ to $C_6$ alkanes. In many embodiments, the hydrocarbon-containing gas feed stream 18 is a methane-containing gas feed stream. The methane-containing gas feed 18 may be a pure methane gas or may be methane gas source containing other gases. In certain instance, the feed stream may be predominantly methane (i.e., >50 mol %) or entirely methane. In particular embodiments, the feed stream may be composed of natural gas (NG), which may have a methane content of from 85 mol % to 97 mol % or more, or other hydrocarbon-rich gases. In some cases the feed stream 18 may be a pretreated feed stream that has been treated to remove undesirable components, such as sulfur-containing compounds. The feed stream 18 may be preheated prior to being introduced into the reactor 12. In particular applications, the feed stream 18 may be heated to a temperature of from 25° C. to 500° C. to improve conversion efficiency or vaporize heavier alkanes. Such preheating may use a heat source that is provided partly or entirely from heat generated during the pyrolysis reactor because the overall process is exothermic. Alternatively, the preheating heat source may be provided from other external sources.

It should be noted in the description, if a numerical value, concentration or range is presented, each numerical value should be read once as modified by the term "about" (unless already expressly so modified), and then read again as not so modified unless otherwise indicated in context. Also, in the description, it should be understood that an amount range listed or described as being useful, suitable, or the like, is intended that any and every value within the range, including the end points, is to be considered as having been stated. For example, "a range of from 1 to 10" is to be read as indicating each and every possible number along the continuum between about 1 and about 10. Thus, even if specific points within the range, or even no point within the range, are explicitly identified or referred to, it is to be understood that the inventor appreciates and understands that any and all points within the range are to be considered to have been specified, and that inventor possesses the entire range and all points within the range.

The stoichiometric ratio for the complete combustion of methane with pure oxygen requires $CH_4/O_2$ mole ratio of 0.5 according to the following exothermic reaction (1) below:

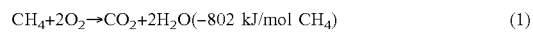
$$CH_4+2O_2 \rightarrow CO_2+2H_2O(-802 \text{ kJ/mol } CH_4) \tag{1}$$

In the present combustion pyrolysis process, a $CH_4/O_2$ or $NG/O_2$ (for natural gas) mole ratio of around 1 to 5 may be used. The excess methane or NG gas serves as "crack gas." The crack gas is converted to $C_2$ and $C_3$ hydrocarbons through endothermic pyrolysis reactions for methane as follows:

$$2CH_4 \rightarrow C_2H_2+3H_2(+188 \text{ kJ/mol CH4}) \tag{2}$$

$$2CH_4 \rightarrow C_2H_4+2H_2(+101 \text{ kJ/mol CH4}) \tag{3}$$

$$2CH_4 \rightarrow C_2H_6+H_2(+32.5 \text{ kJ/mol CH4}) \tag{4}$$

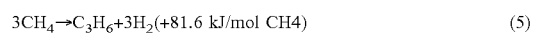
$$3CH_4 \rightarrow C_3H_6+3H_2(+81.6 \text{ kJ/mol CH4}) \tag{5}$$

$$3CH_4 \rightarrow C_3H_8+2H_2(+40.2 \text{ kJ/mol CH4}) \tag{6}$$

Due to the highly endothermic nature of the pyrolysis reactions, the combustion pyrolysis process requires high temperature, usually above 1500° C., in order to achieve a high yield of $C_2+$ hydrocarbons. The pyrolysis reaction occurs without the presence or need of a catalyst. The thermal energy at this high temperature is supplied by the unique pyrolysis burner and feed assemblies of the pyrolysis reactor, as is discussed in more detail later on.

The pyrolysis product gases 20 may contain $C_2+$ hydrocarbons, in which acetylene is the main product, as well as synthesis gas (carbon monoxide and hydrogen). The pyrolysis gases need to be quenched within a few milliseconds downstream, typically less than 10 millisecond, in order to minimize the formation of heavy hydrocarbons and soot. This can be achieved by a short residence time in the hot temperature zone of the reactor 12 due to their high velocity, followed by quenching in a quenching unit 22, such as a water-droplet-spray quench vessel, or other suitable gas quench devices.

The quenched products 24 may be delivered to a separation unit 26, where the pyrolysis product gases are separated to form a product stream 28 containing a high concentration of acetylene gas ($C_2H_2$), which can be further used for various acetylene byproducts using Reppe chemistry or reformed in a hydrogenation unit 30 to produce hydrogenated products, such as ethylene and other products 32. A portion of the separated pyrolysis process gas 34, which is typically composed of $CH_4$ and other alkanes, may be recycled to the pyrolysis reactor 12 for higher conversion and yield performance Synthesis gas 36 may also be separated in the separation unit 26 from the process gas for chemical production and power generation usage.

It should be noted that while the system 10 of FIG. 1 shows single units for the various process steps, each unit could be composed of one or more units that may operate in conjunction with one another, such as parallel or sequentially, to carry out the various process steps described.

Figure 2:
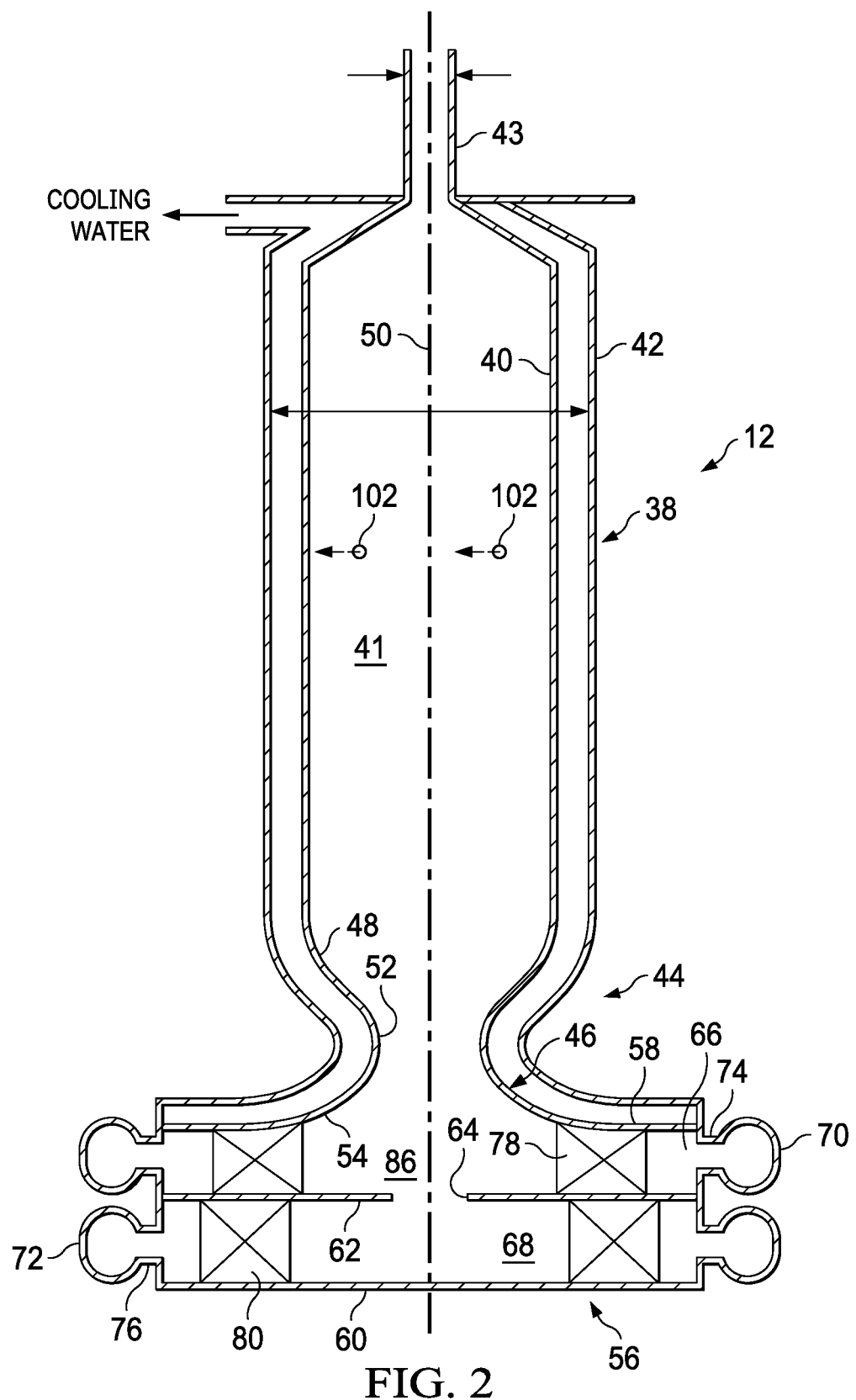
FIG. 2 is a schematic representation of a pyrolysis reactor shown in cross section, constructed in accordance with particular embodiments.

Referring to FIG. 2, an elevational cross-sectional schematic representation of the pyrolysis reactor 12 for pyrolysis of hydrocarbon gases, such as methane or natural gas, is shown. The pyrolysis reactor 12 includes a reactor vessel 38 having a reactor wall 40 that defines a reaction chamber 41. The reactor wall 40 may have a cylindrical configuration with a constant diameter along all or a portion of its length, which may constitute a majority of its length. In most instances, the reactor 12 is oriented vertically so that the cylindrical reactor wall 40 is oriented in an upright orientation. The reactor can have other orientations (e.g., horizontal, sloped, etc.), however, because the process is controlled by the centrifugal force, which exceeds the gravitational force by a few orders of magnitude. The reactor vessel 38 may be configured to provide a length to diameter ratio (L/D) of at least 2. In particular applications, the L/D ratio may range from 2-5.

The reactor vessel 38 may be formed from steel. In certain embodiments, a cooling jacket can be provided around the reactor vessel, wherein a second steel wall 42 is positioned around and spaced from the inner reactor wall 40 and a cooling fluid, such as water may be circulated through the jacket formed between the walls 40, 42. In other embodiments, the reactor wall 40 may be formed from one or more layers of refractory material that line the interior of an outer steel wall to reduce heat loss and sustain the high temperatures of the reactor 12. As will be described later on, because of the unique design and operation of the reactor 12, the reactor wall 40 is cooled internally by the high-velocity near-wall gas flow pushed by centrifugal forces against the reactor wall 40 so that in some applications no exterior cooling jacket is required. This also allows refractory materials to be used for the interior of the reactor wall 40. Refractory materials (without cooling) typically cannot be used with conventional pyrolysis reactors due to the high heats encountered.

An outlet 43 is provided at the upper or downstream end of the reactor vessel 38 for removing or discharging pyrolysis products from the reaction chamber 41. Although the outlet 43 is shown located at the upper end of the reactor vessel 38, in other embodiments it may be located at the lower end of the reactor vessel 38, so that the flow through the reactor is in the opposite direction (i.e., from top to bottom). The outlet diameter can be same as the diameter of the reactor wall 40 or the outlet diameter may be reduced to accelerate the flow before quenching and collection downstream.

The reactor 12 includes a burner assembly 44 that is coupled to the lower or upstream end of the reactor wall 40 of the reactor vessel 38. The burner assembly 44 has a burner conduit 46 with a circumferential wall 48 that surrounds a central longitudinal axis 50. Where the reactor 12 is oriented vertically, the central axis 50 will also be oriented vertically as well and will be concentric with or parallel to a central vertical axis of the reactor vessel 38. In the embodiment shown, the axis 50 is concentric with and aligned with the central longitudinal axis of the reactor vessel 38. The circumferential wall extends from opposite upstream and downstream ends of the burner conduit 46. As can be seen in FIG. 2, the circumferential wall 48 smoothly tapers in width or diameter from the downstream and upstream ends to an annular constricted neck portion 52 located between the downstream and upstream ends of the burner conduit 46. The interior of the circumferential wall 48 may have a circular perpendicular cross section (with respect to the axis 50) along its length. The circumferential wall 48 interior defines a flow path of the burner assembly 44 with the constricted neck portion 52 forming a converging-diverging streamlined nozzle of the burner assembly 44. The nozzle geometry of the neck portion 52 is configured based upon the theory relating to swirling conical jets of a viscous incompressible fluid described in detail later on.

The circumferential wall of the burner conduit from the downstream end where it joins reactor wall 40 to the annular constricted neck portion 52 may, in some embodiments, be configured as a smooth, continuous concave wall having an ellipsoidal cap or spherical cap shape or configuration. Likewise, the upstream portion of the reactor wall 40 of the pyrolysis reaction chamber 41 that joins the circumferential wall of the burner conduit may also be configured as a smooth, continuous concave wall that follow contour lines of an ellipsoidal cap or spherical cap shape or configuration.

The downstream end of the burner conduit 46 joins the reactor wall 40 around its perimeter so that the burner conduit 46 is in fluid communication with the reactor chamber 41 of the pyrolysis reactor vessel 38. The upstream end of the burner conduit 46 forms a burner assembly inlet 54.

A pyrolysis feed assembly 56 is provided with the reactor 12. The pyrolysis feed assembly is in fluid communication with the inlet 54 of the burner assembly 44, with the central axis 50 passing through the pyrolysis feed assembly 56. The feed assembly 56 includes a downstream feed assembly wall 58 that extends circumferentially around and joins the upstream end of the burner assembly inlet 54. The feed assembly wall 58 is oriented perpendicularly or substantially perpendicularly (i.e., ≤5 degrees from perpendicular about its circumference) to the central axis 50.

Axially spaced upstream from the downstream wall 58 along the central axis 50 is an upstream feed assembly wall 60. The upstream wall 60 is perpendicular to or substantially perpendicularly (i.e., ≤5 degrees from perpendicular about its circumference as it extends from the central axis) to the central axis 50 and extends across the central axis 50.

A gas partition wall 62 is axially spaced between the downstream and upstream feed assembly walls 58, 60. The partition wall 62 is also oriented perpendicularly to or substantially perpendicularly (i.e., ≤5 degrees from perpendicular about its circumference as it extends from the central axis) to the central axis and has a central opening 64 that surrounds the central axis 50 and is concentric with the burner conduit 46. The central opening 64 has a circular configuration. Other shapes for the central opening 64 (e.g., oval) may also be used provided such configuration facilitates the swirling of gases to provide the required flow patterns described herein. This shape may also correspond to the cross sectional shape of the circumferential wall 48 of the burner conduit 46. In most applications, however, the central opening 64 will be circular in shape. The central opening 64 may have a diameter or width that is the same or slightly different than the diameter or width of the constricted neck 52 of the burner conduit 46 at its narrowest point.

The partition wall 62 defines an annular gas flow space 66 located between the downstream feed assembly wall 58 and the downstream side of the partition wall 62. Likewise, an annular gas flow space 68 is defined by the upstream side of the partition wall 62 and the upstream feed assembly wall 60. This provides flow passages through which hydrocarbon gas feed to be pyrolyzed (e.g., $CH_4$ or natural gas) and oxygen gas can be separately introduced and passed through the flow spaces 66, 68, respectively, perpendicularly or substantially perpendicular to the central axis 50 of the burner conduit 46. In most cases, the upper or downstream flow space 66 will constitute a hydrocarbon gas inlet flow space for introducing an oxygen-containing gas and the lower or upstream flow space 68 will constitute an oxygen gas inlet flow space for introducing an oxygen-containing gas. This configuration enhances mixing since the centrifugal force presses the higher-density oxygen into the lower-density hydrocarbon (e.g., methane).

The walls 58, 60, and 62 forming the flow spaces 66, 68 are axially spaced apart to provide the desired volume and flow characteristics for the gases flowing therethrough. This may be based upon the desired flow rates or linear velocities of each of the hydrocarbon and oxygen feed gases and their relative amounts. For instance, the relative volume of oxygen gas needed for the combustion is typically less than that of the hydrocarbon feed gas needed for the combustion and pyrolysis. Therefore, the partition wall 62 may be spaced closer to the upstream wall 60 so that the hydrocarbon gas flow space 66 is larger to accommodate the greater flow of hydrocarbon gas.

Annular gas manifolds 70, 72 provided around the periphery of the flow spaces 66, 68 are fluidly coupled to a hydrocarbon-containing-gas source and an oxygen-containing-gas source, respectively. The manifolds 70, 72 are provided with the pyrolysis feed assembly 56 to facilitate introduction of feed gases into the flow spaces 66, 68. Gas inlets 74, 76 from the manifolds 70, 72 may be directed tangentially into the flow spaces 66, 68 so that the gases are not directed only radially toward the central axis 50 from the inlets 74, 76, but instead are directed mostly tangentially around the central axis to provide an inwardly spiraling flow pattern. Furthermore, the walls 58, 60, 62 of the feed gas assembly keep the gases introduced from the manifolds 70, 72 from flowing axially along the central axis 50 while they are contained within the flow spaces 66, 68. The manifolds 70, 72 can be configured as standard manifolds (e.g., snail-like) as may be typically used in vortex devices.

Figure 3:
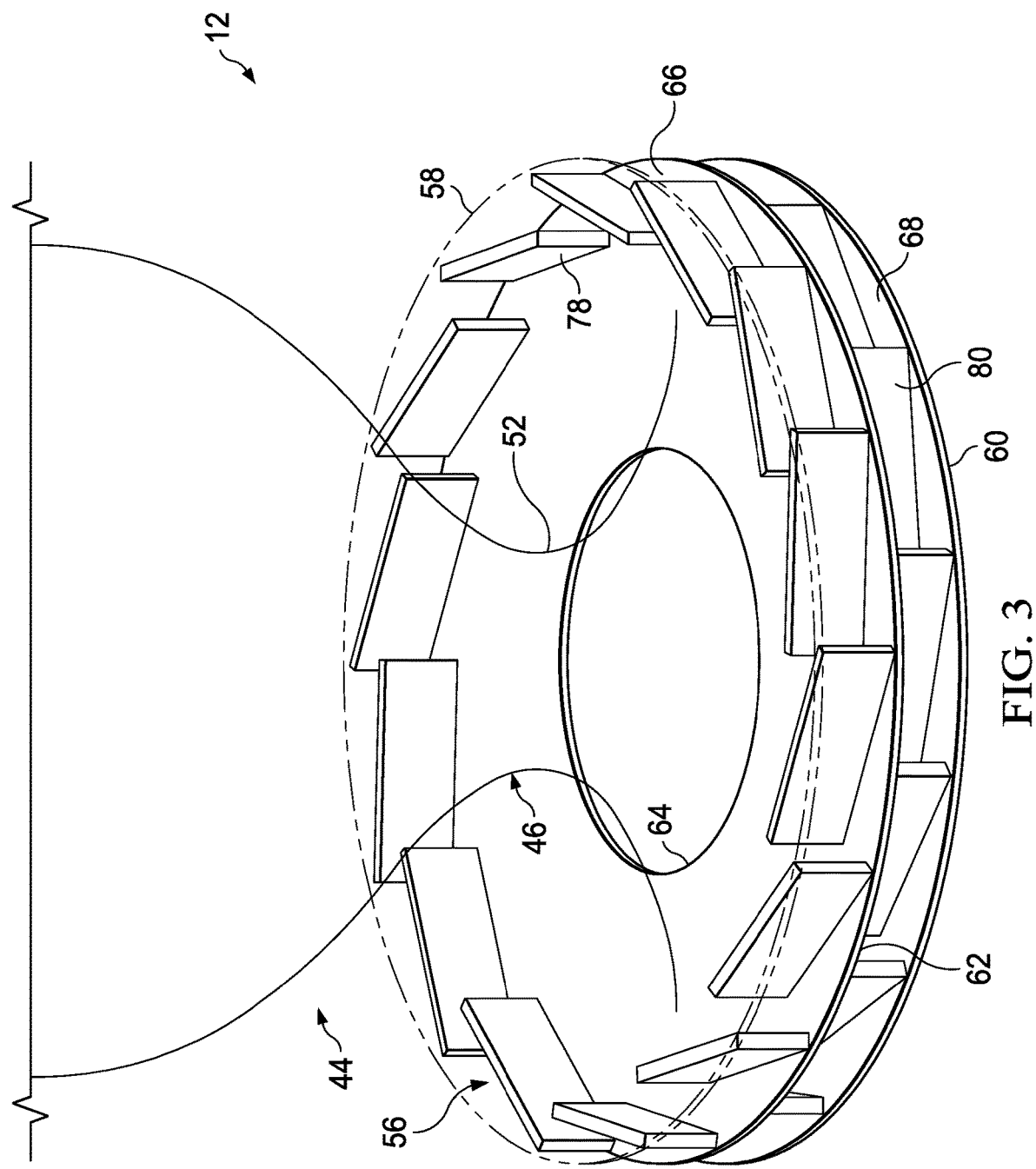
FIG. 3 is perspective view of lower portion of the pyrolysis reactor of FIG. 2, showing a burner assembly and pyrolysis feed gas assembly constructed in accordance with particular embodiments.

Referring to FIG. 3, one or both of the flow spaces 66, 68 may be provided with a plurality of circumferentially spaced guide vanes 78, 80 (e.g., 10 to 60 guide vanes). Each guide vane 78, 80 may be a planar member that is oriented in a plane that is parallel to the central axis and extends between the walls 58, 60 and the partition wall 62. The guide vanes 78, 80 may be circumferentially spaced an equal distance from one another. In certain embodiments, the guide vanes 78, 80 may be fixed in place, with the upper and lower side edges of the guide vanes being joined along their lengths or a portion of their lengths to the walls 58, 60, 62 so that there are no air gaps between the side edges of the vanes 78, 80 and the walls 58, 60, 62. In other embodiments, however, the guide vanes are movable. In such cases, the upper and lower side edges of the vanes 78, 80 may be closely spaced from the walls 58, 60, 62 to provide a small clearance to allow such movement but that minimizes air gaps where gases may pass through. Seals may also be used to effectively close these spaces or clearances. In other instances, the vanes 78, 80 may be oriented so that the plane of the vane is in a non-parallel or slanted orientation relative to the central axis. In such cases, the side edges may be fixed to the walls 58, 60, 63 or remain closely spaced from walls 58, 60, 62 to minimize air gaps for gasses to pass through. In other instances, the guide vanes 78, 80 may be configured as airfoils having curved surfaces, which may be oriented with the width being parallel or non-parallel to the axis 50, to provide desired flow characteristics.

The guide vanes 78, 80 are provided adjacent to the outer perimeter of the flow spaces 66, 68 and are spaced in an annular or circular ring pattern near the manifold inlets 70, 72, respectively, although they may be provided in an annular pattern at other positions located radially inward or further within the interior of the flow spaces 66, 68, or one or more additional annular sets of guide vanes may be located radially inward from that located along the outer periphery to facilitate inwardly spiraling fluid flow.

Feed gases from the manifolds 70, 72 are delivered nearly tangentially to the outer perimeter of the flow spaces 66, 68, where the guide vanes 78, 80 further facilitate directing the gas flow in an inwardly swirling or spiraling fluid flow pattern within the flow spaces 66, 68. In other embodiments, the guide vanes 78, 80 may impart the full tangential flow of the introduced gases in cases where the gas from inlets 74, 76 may be directed radially toward the central axis 50. In such cases the guide vanes 78, 80 prevent flow directly toward the central axis 50 and direct the flowing gases tangentially to provide the inwardly swirling or spiraling fluid flow pattern.

The guide vanes 78, 80 of each flow space 70, 72 may be mounted on actuators (not shown) so that they can be selectively movable to various positions to provide a selected inwardly spiraling flow pattern. The guide vanes 78, 80 may be pivotal about an axis that is parallel to the central axis 50 so that the vanes 78, 80 may be moved to various positions.

Figure 4:
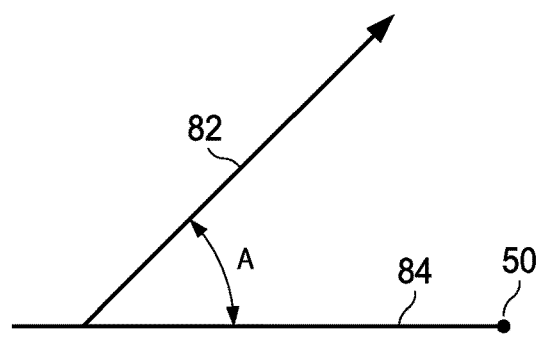
FIG. 4 is schematic showing the angle of guide vanes of a pyrolysis feed gas assembly of the pyrolysis reactor of FIG. 2 relative to a central longitudinal axis of a burner assembly of the reactor, in accordance with particular embodiments.

The orientation of the vanes 78, 80, as well as the orientation of the tangential inlets 74, 76 may be seen in FIG. 4. As shown, the line 82 represents the angle of orientation of the vanes 78, 80 and/or inlets 74, 76 with respect to the radial line 84 extending radially from the central axis 50. Angle A is the angle between the tangential line 82 and the radial line 84. In particular embodiments, the angle A may range from 50° to 85°, more typically from 60° to 75°. Thus, the vanes 78, 80 may be permanently oriented at an angle A within this range or may be movable to various angular orientations within this range. In most cases, each of the vanes 78, 80 within the annular pattern will be set at the same angle A and when actuated will move in unison or close to unison to the same angle A to provide the desired spiraling fluid flow characteristics. The angle(s) of orientation A of the vanes 78 and/or inlets 74 of flow passage 66 may be the same or different than the angle(s) of orientation of the vanes 80 or inlets 76 of flow passage 68.

In most cases, the tangential gas inlets 74, 76 and/or the guide vanes 78, 80 will be oriented to provide spiraling fluid jet flow that is in the same rotational direction about the axis 50, i.e., clockwise or counter-clockwise. Thus, both the hydrocarbon-containing gas and the oxygen-containing gas will both spirally flow clockwise or counterclockwise about the axis 50 within the flow spaces 66, 68.

Referring again to FIG. 2, the area extending from the central opening 64 of the partition wall 62 to the burner assembly inlet 54 define a mixing chamber 86 of the pyrolysis feed assembly 56. It is here that gases from the flow space inlets 66, 68 are discharged and are mixed within the mixing chamber 86 to form a swirling gas mixture within the mixing chamber 86. This swirling gas mixture then passes through the burner conduit 46 and into the reaction chamber 41 of the reactor vessel 38.

As discussed previously, the gas flow space 66 will typically be used to introduce a spiraling jet of hydrocarbon-containing gas into the mixing chamber 86. This may be an alkane-containing gas, such as methane or natural gas. The flow space 68, which is located upstream or below the flow space 66, will typically be used to introduce a spiraling jet of oxygen-containing gas. The hydrocarbon and oxygen gases are introduced separately from one another into the flow spaces 66, 68 and not as mixture, which could cause safety issues.

As the spiraling jet gases from flow spaces 66, 68 flow radially inward, they are discharged into the mixing chamber 86 where the hydrocarbon gases and oxygen gases are mixed. The swirling gas mixture then passes axially through the burner conduit 46, with at least a portion of the swirling gas mixture forming a thin, annular alkane-rich gas flow layer immediately adjacent to the burner conduit 46. A portion of the swirling gas mixture is combusted as the swirling gas mixture passes through the burner conduit to provide conditions suitable for pyrolysis of the hydrocarbon gases, such as methane or light alkane gases, within the pyrolysis reaction chamber 41 of the reactor vessel 38, with a portion of the hydrocarbon gases being converted to pyrolysis products within the pyrolysis reaction chamber 41.

The oxygen gas has a higher molecular weight than the methane gas, which would be typically used as a pyrolysis feed gas. Furthermore, the hydrocarbon-containing gas is typically preheated, whereas the oxygen-containing gas may not be, so that the methane- or other alkane-containing gas is less dense or lighter than the oxygen-containing gas. Thus, as the oxygen-containing gas is discharged as a spiraling jet from flow space 68 it will move into the lighter hydrocarbon-containing gas through the central opening 64 into the mixing chamber 86. Centrifugal forces push the jetted oxygen gas into the surrounding hydrocarbon or methane gas jet. This enhances mixing of the two streams. In addition, the hydrocarbon gas from flow space inlet 66 and oxygen gas from flow space inlet 68 typically have different velocities. This can create a shear layer between the gases that is subject to the Kelvin-Helmholtz instability to further enhance mixing of the gases.

Additionally, the oxygen, as it is mixed with the methane or hydrocarbon gas, will generally remain encapsulated by a surrounding swirling portion of the discharged spiraling jet of hydrocarbon gases within the center of the mixing chamber 86. The oxygen gas will thus be enclosed or surrounded by the swirling hydrocarbon gases as it passes through the burner conduit 46. This is due to the fact that the combusted mixture is several times lighter than the incoming hydrocarbon gas and the centrifugal forces push the hydrocarbon gas to the burner/reactor walls (52, 48).

Figure 5:
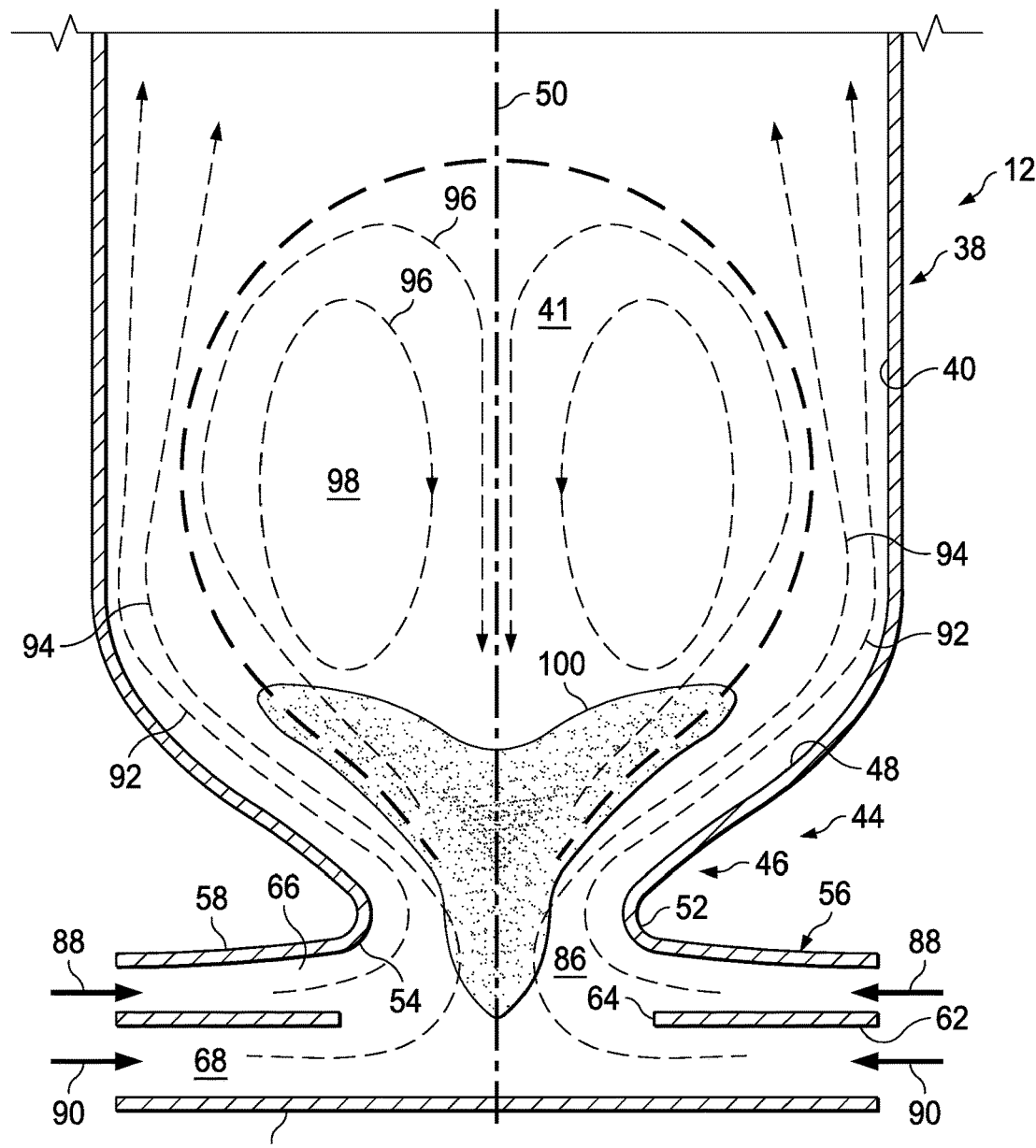
FIG. 5 is a schematic of the pyrolysis reactor of FIG. 2 showing gas flows within the reactor.

This can be seen schematically in FIG. 5 where the reactor 12 is shown. As shown, methane feed 88 is introduced nearly tangentially into flow space 66 and oxygen gas 90 is separately introduced nearly tangentially into flow space 68 to create inwardly spiraling jet flow where the gases mix within the mixing chamber 86. The dashed lines 92, 94 generally show the overall through-flow path of the methane feed 88 and oxygen 90.

Figure 10:
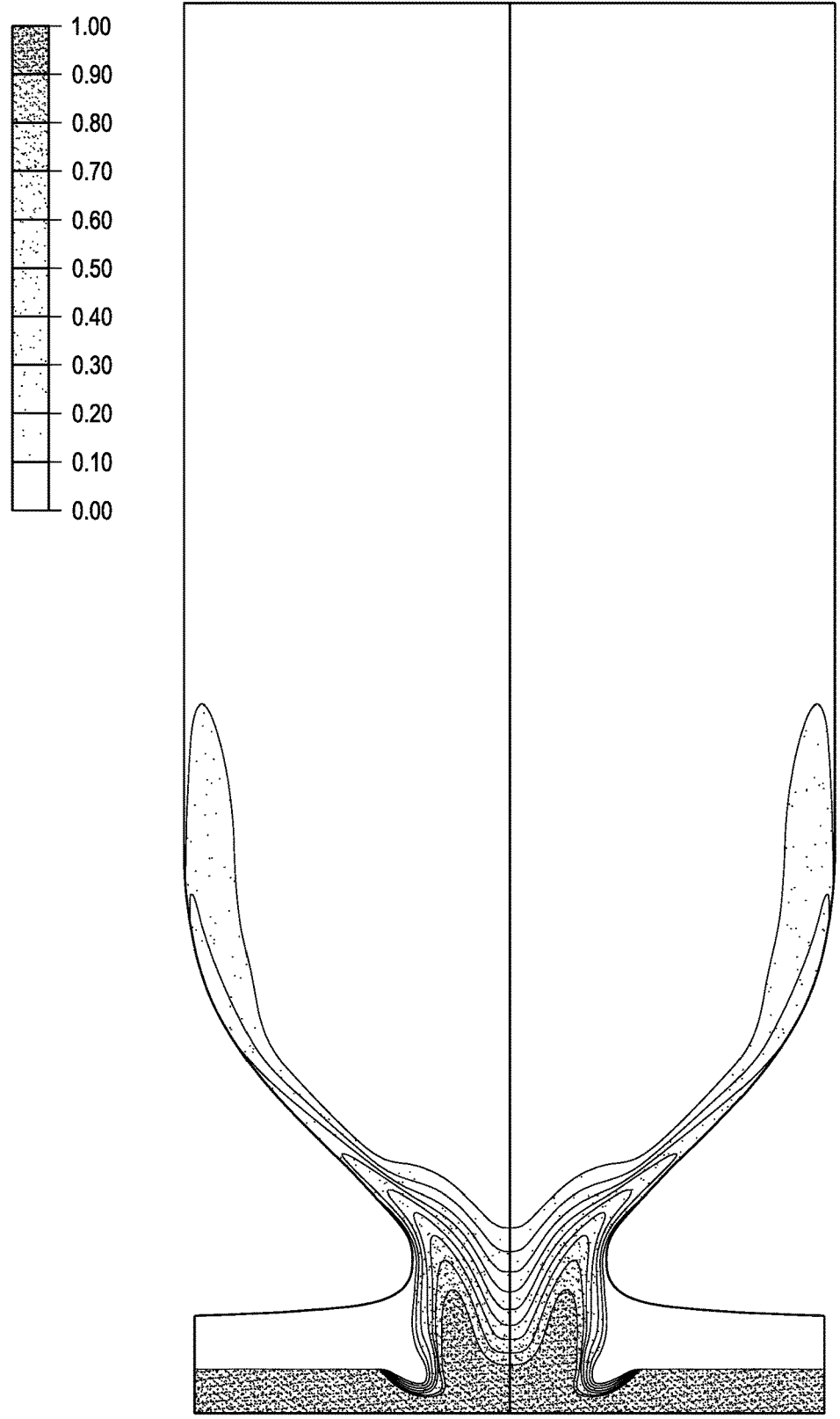
FIG. 10 is a representation of mass fraction distribution for oxygen gas of the lab scale pyrolysis reactor unit of Example 1.

As can be seen in FIG. 5 and FIG. 10 (discussed in more detail later on), while mixing occurs within the mixing chamber 86, a portion of the methane feed exists as an outer non-mixed layer of swirling methane feed 92 that remains exterior to the oxygen flow 94 as it mixes with the remaining methane and passes through the burner assembly 44. At least a portion of the swirling gas mixture forms a thin, annular mixed gas flow layer immediately adjacent to the burner conduit 46, as can be seen in FIG. 10. A portion of the swirling gas mixture is combusted as the swirling gas mixture passes through the burner conduit 46 to provide conditions suitable for pyrolysis of the hydrocarbon gases, such as methane or light alkane gases, within the pyrolysis reaction chamber 41 of the reactor vessel 38. Such conditions include temperatures of from 2700° C. to 2850° C. within the reaction chamber 41, where pyrolysis reactions take place.

As the combustion gases are formed they are at a much higher temperatures (approaching 2850° C.) and will thus be lighter than the cooler incoming pressurized non-combusted hydrocarbon and oxygen gases. The centrifugal forces of the swirling gases provide a stable stratification of density, where the higher-density hydrocarbon gases (e.g., methane), as well as any non-combusted oxygen gases, are pushed as a thin layer 92, 94 towards the sidewall 40 (FIG. 5) of the reactor vessel 38. This occurs while the centrifugal buoyancy pushes the hot flue or combustion gases toward the axis 50. The thermal stratification wherein the cooler gases are pushed outward as at 92, 94 protects the sidewalls 40 of the reactor vessel 38 from overheating. The device geometry and the gas-mixture swirl also result in a back flow of combustion or flue gases 96 formed from the combustion of the gas mixture within the reaction chamber 41 that flows upstream and radially inward from the thin, annular mixed gas flow layers 92, 94, that circulate within the reaction chamber 41, as shown in FIG. 5, to form recirculation zone 98. This recirculation also forms and stabilizes the burner assembly flame 100 so that it is compact and remains close to the downstream end of the burner conduit 46, resulting in better and complete combustion.

Referring to FIG. 2, in operation, a hydrocarbon-containing gas is introduced from manifold 70 to tangential inlets 74 into flow space 66. The hydrocarbon-containing gas may be methane, natural gas, light-alkane gases (e.g., $C_2$-$C_6$), etc. An oxygen-containing gas, which may be a concentrated or pure oxygen gas, such as from the air separation unit 16, is introduced though manifold 72 through inlets 76 into the flow space 68. In certain applications, for methane or natural gas (NG), the mole ratio of $CH_4/O_2$ or $NG/O_2$ may range from 1 to 5, more particularly from 1 to 4, and still more particularly from 1.5 to 2.5, and even still more particularly from 1.8 to 2. Such ratio may depend upon the particular operating conditions and desired products to be formed. The gas feed streams may be introduced to provide different flow velocities to provide the Kelvin-Helmholtz instability for enhanced mixing. The flow velocities may range from 10 to 500 m/s, more particularly from 100 to 400 m/s. The reactor 12 may be operated at from 100 kPa to 20,000 kPa, with a gas residence time within the reactor of from 10 to 10,000 microseconds.

The gases are introduced and flow through the flow spaces 66, 68 so that the axial velocity (i.e., relative to the axis 50) is zero prior to being discharged into the mixing chamber 86. The tangential inlets 74, 76 and/or the orientation of the guide vanes 78, 80 may be set for each flow space 66, 68 so that a selected azimuthal-to-radial velocity for each of the feed streams that flow through the flow spaces 66, 68 is achieved. With respect to the azimuthal-to-radial velocity, in particular embodiments, this may range from 0 to 30 or more, more particularly from 0, 1, or 2 to 3, 4, 5, 6, 7, 8, 9, 10, 11, 12, 13, 14, 15, 16, 17, 18, 19, 20, 21, 22, 23, 24, 25, 26, 27, 28, 29, or 30. In some applications the azimuthal-to-radial velocity may range from 0 to 5, more particularly from 2 to 4. The particular azimuthal-to-radial ratio may vary depending upon the particular reactor configuration and composition of the hydrocarbon/oxygen streams, however.

Pyrolysis products produced in the reactor are removed from the reactor vessel 38 through outlet 43, where they may be quenched and further processed and recycled, as discussed with respect to the process steps previously described for FIG. 1.

In a variation of the pyrolysis reactor described, additional hydrocarbon feed gas (e.g., methane, natural gas, etc.) can be introduced at an intermediate position along the length of reactor vessel, such as at inlet 102 (FIG. 2). One or more such inlets 102 may be provided at various locations and in the reactor vessel 38, which may be circumferentially and longitudinally spaced apart. The inlets 102 may be oriented or configured so that gases are introduced tangentially, as well, to facilitate swirling fluid flow, similar to that delivered from the feed assembly 56.

In some embodiments, a plurality of burner assemblies and corresponding pyrolysis feed assemblies can be provided in a single reactor while maintaining the high performance.

The reactor design described herein features high methane conversion and selectivity, higher overall $C_2$+ yield than other conventional single-stage or two-stage acetylene production methods. The reactor is relatively simple in configuration, which significantly reduces the capital and operating costs. The high-swirling burner provides stable and compact non-premixed combustion, resulting in cooler reactor wall temperatures facilitated by the high-speed annular flow of the methane adjacent the reactor wall. The reactor can be scaled up by increasing feeding rate and dimension scale up.

The following examples serve to further illustrate various embodiments and applications.

EXAMPLES

In the following examples, Computational Fluid Dynamics (CFD) simulations, using commercial software available as the ANSYS FLUENT® software product, were conducted for the optimal design of a pyrolysis reactor, as has been described herein, to verify its performance by numerical experiments. The swirling fluid flow, heat transfer, and detailed gas phase reactions were modeled in a two-dimensional axisymmetric CFD framework using Reynolds Averaged Navier-Stokes (RANS) approach using Reynolds Stress turbulence model. The modeled base case ANJEVOC-CP reactor has an inner diameter of about 6 inch, with a methane/oxygen molar ratio of 1.8-2.0.

Example 1

Figure 6:
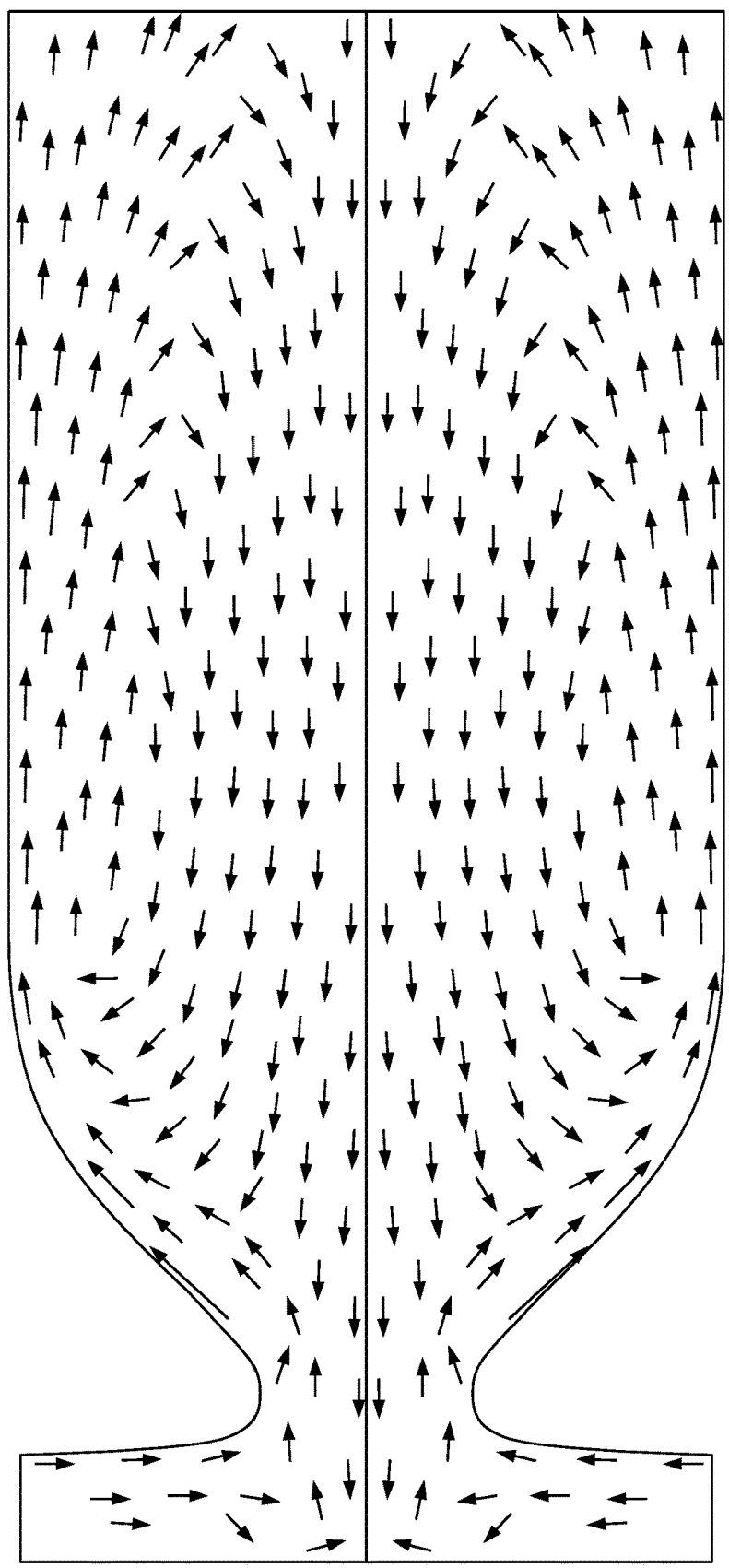
FIG. 6 is representation of the pyrolysis reactor geometry and velocity vectors showing the direction of gas flow in a lab scale pyrolysis reactor unit model of Example 1.
Figure 7:
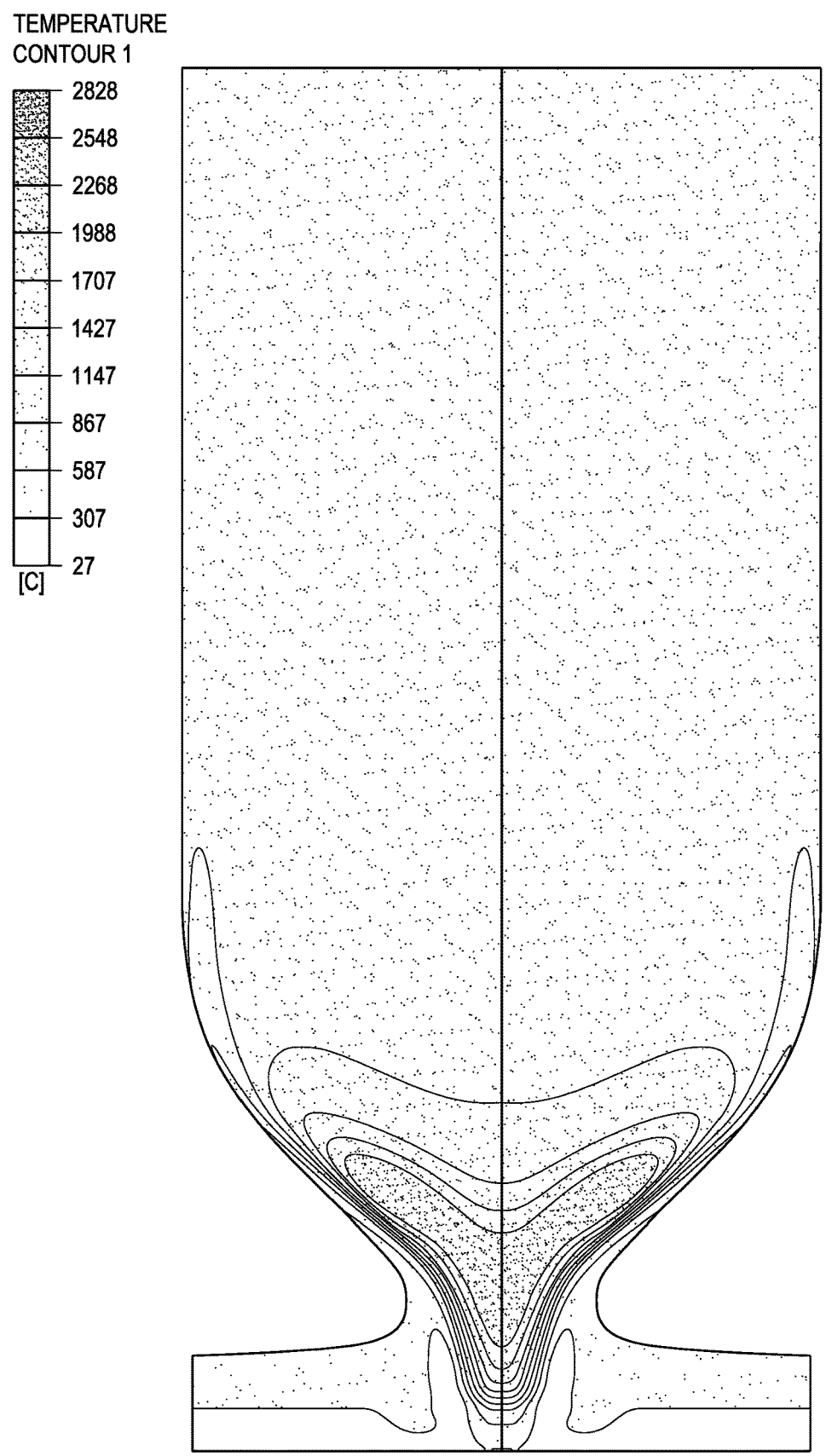
FIG. 7 is a representation of the temperature distribution of the lab scale pyrolysis reactor unit of Example 1.

FIG. 6 shows the pyrolysis reactor geometry and axial-velocity distribution in a lab scale unit model. The areas arrow direction indicate flow direction of the gas phase, and its length indicates the relative magnitude of the velocity. At the feed assembly inlet, the axial velocity is zero, the radial and the azimuthal velocity are uniform and the azimuthal-to-radial velocity ratio is three for both $O_2$ and $CH_4$. This highly swirling flow forms a recirculation region near the axis of the reactor as described above in FIG. 5, which stabilizes the flame and enhances the mixing while burning. This backflow (reverse flow region in reaction chamber near the axis in FIG. 6) presses the combustion to the nozzle neck. This can be seen in FIG. 7, where the darker regions downstream from the burner conduit indicate higher temperatures and the lighter regions indicating cooler temperatures. The backflow of gases presses the combustion to the burner conduit constriction in the darker high-temperature region (the maximal temperature is 2800° C.) depicted as the dark tri-pointed shape in FIG. 7 located at and near the burner assembly. It also shows that the hot region is located near the central axis and the hot combustion gases are separated from the sidewall of the burner conduit by the thin annular jet (lighter region) layer, which prevents the sidewall from overheating.

Figure 8:
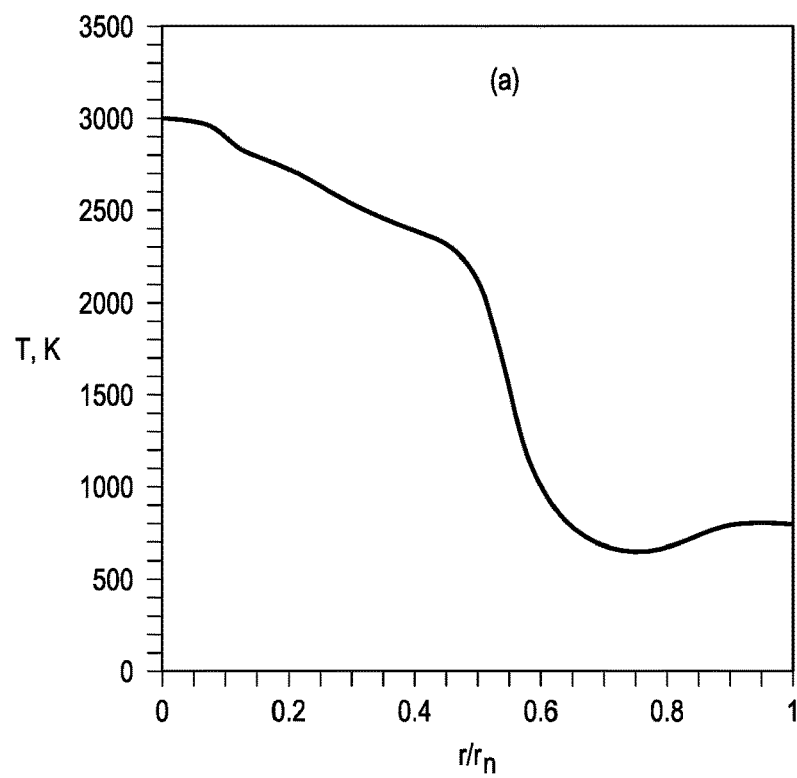
FIG. 8 is a plot of the temperature profile in relation to the radial distance from the device axis of a constricted neck portion of a burner conduit of the lab scale pyrolysis reactor of Example 1, where $r_n$ is the neck radius.
Figure 9:
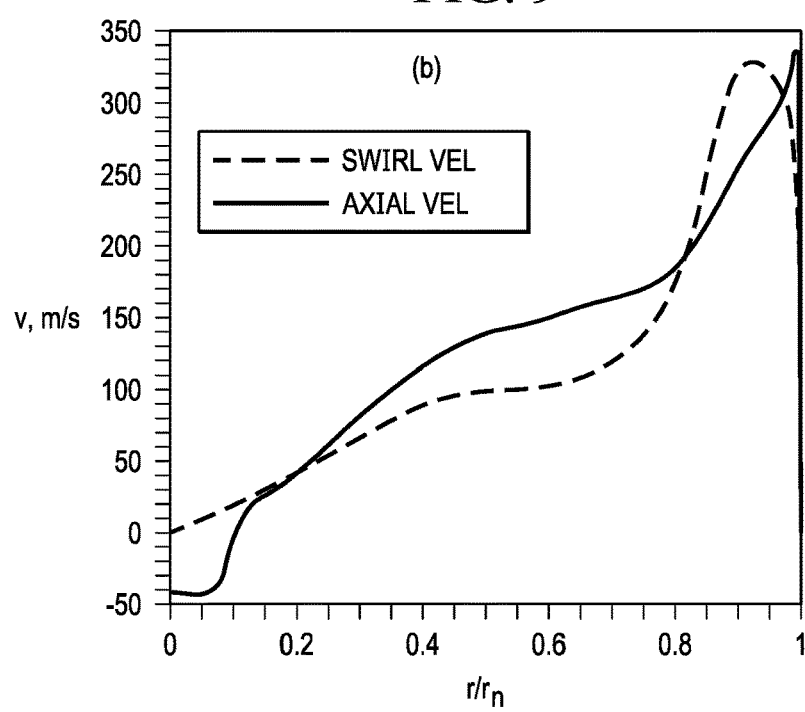
FIG. 9 shows a plot of the axial and swirl velocity in relation to the radial distance from the device axis of a constricted neck portion of a burner conduit of the lab scale pyrolysis reactor of Example 1, where $r_n$ is the neck radius.

FIGS. 8 and 9 illustrate the wall protection from overheating by the annular swirling jet in greater detail by showing the radial profiles of temperature and velocity at the nozzle neck. The maximal temperature, achieved in the combustion region at the axis (r=0), is 3004° K. FIG. 8 shows that the temperature drops down to 805° K at the sidewall, where $r=r_n$ (i.e., $r/r_n=1$); $r_n$ is the neck radius.

In FIG. 9 the sharp peak of the axial velocity (337 m/s) near the sidewall shows the high-velocity jetting behavior. This high-speed annular jet, transporting the most mass flux of the cooler $CH_4$, protects the sidewall of the reactor from overheating. The jet is pressed to the sidewall by the centrifugal force provided by the high-speed swirl velocity whose near-sidewall peak is 327 m/s.

Figure 11:
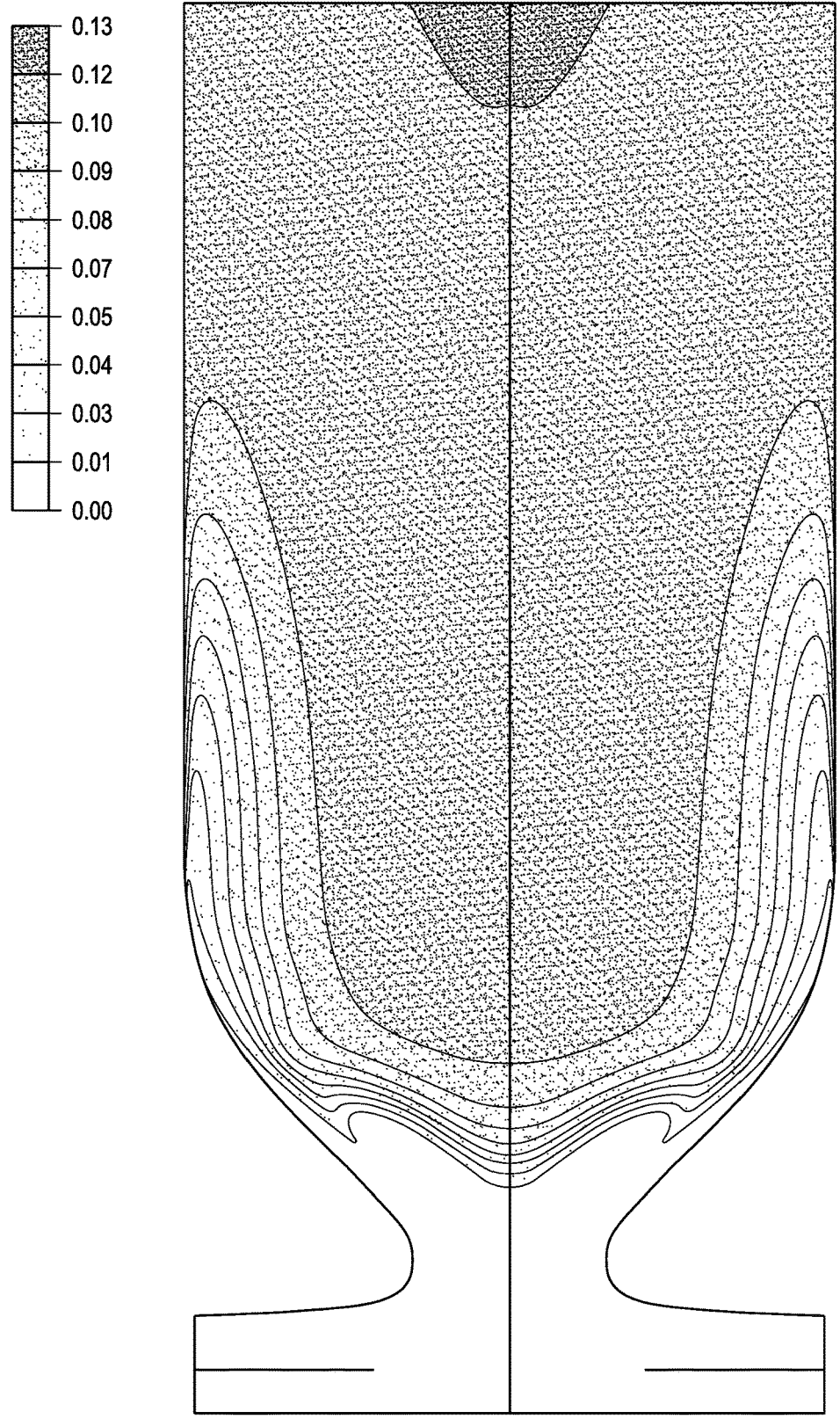
FIG. 11 is a representation of mass fraction distribution for acetylene ($C_2H_2$) of the lab scale pyrolysis reactor unit of Example 1.

FIG. 10 depicts distributions of oxygen and FIG. 11 depicts acetylene ($C_2H_2$) formation from the pyrolysis of methane in the reactor. In FIG. 10, the oxygen concentration is shown at its highest in the flow space to the far bottom, upstream from the burner assembly, which appears as a dark region within the flow space. From there moving downstream, the oxygen concentration decreases, as shown by the two-pronged forked area flowing out of the oxygen flow space and directed towards the burner assembly and the lighter areas emanating from the burner where the oxygen is mixing with methane. The lighter areas in the downstream methane-containing flow space, the very thin light area along the sidewalls of the burner conduit and along the upstream end of the reactor, as well as the majority of the reaction chamber of the reactor downstream of the burner assembly indicate a lack of oxygen. Thus, oxygen is totally consumed by combustion in the burner assembly, while the cylindrical part of the reaction chamber is practically oxygen-free.

In FIG. 11, the lighter areas to the bottom or upstream in the reactor near the burner assembly indicate a low mass fraction of $C_2H_2$. The darker areas to the top or downstream of the reactor indicate an production of $C_2H_2$ concentration from the pyrolysis of methane. As can be seen when comparing FIGS. 10 and 11, $C_2H_2$ is absent where $O_2$ presents and $C_2H_2$ is mostly produced in the cylindrical reaction chamber of the reactor. Therefore, the burner assembly serves as a compact non-premixed burner and the cylindrical part of the reactor facilitates pyrolysis.

Example 2

Figure 12:
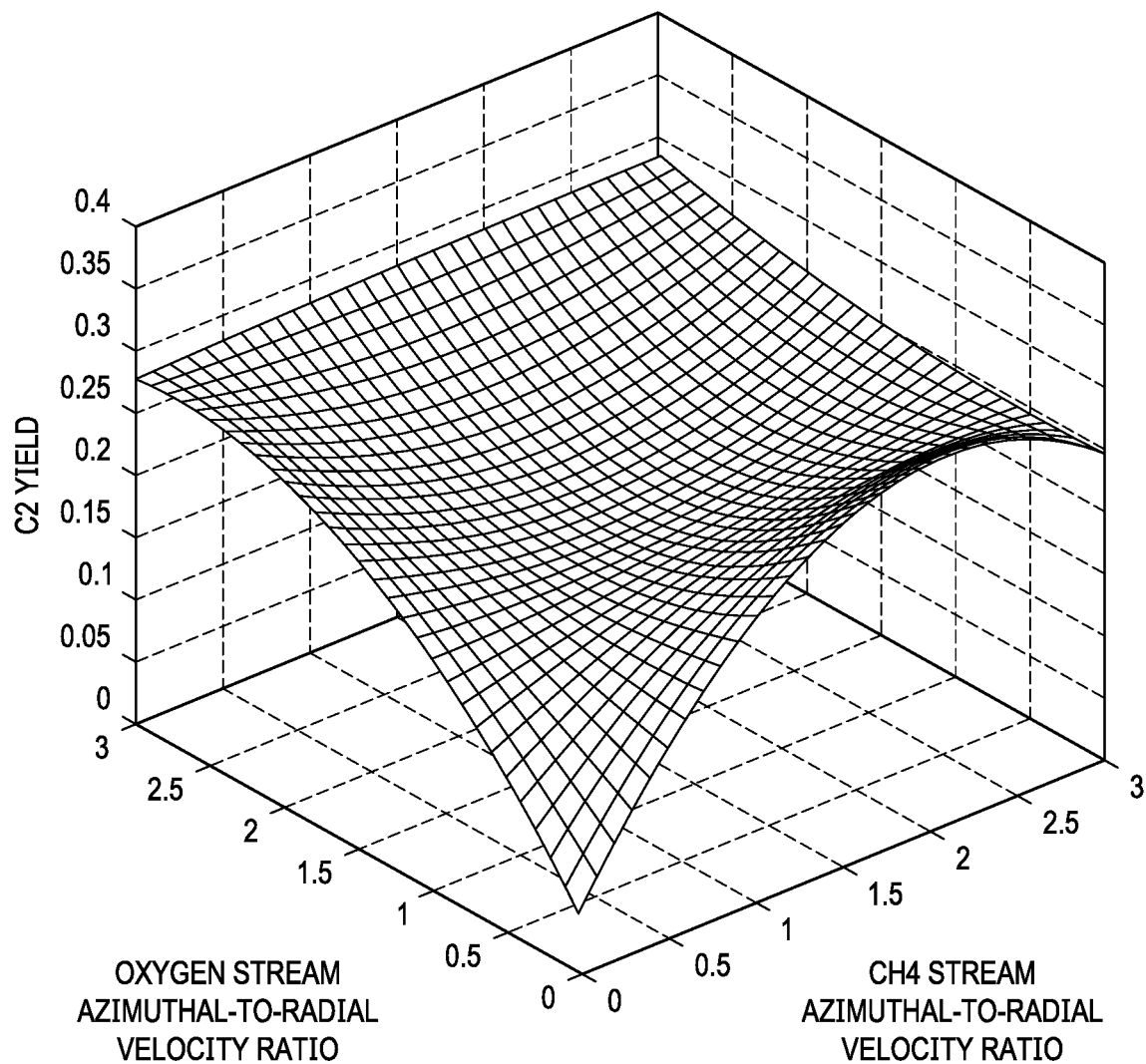
FIG. 12 is a 3-dimensional plot of the effect of azimuthal-to-radial velocity ratios for each of methane and oxygen gas feeds and the resulting yield of acetylene ($C_2H_2$) in a lab scale pyrolysis reactor unit model of Example 2.

FIG. 12 shows the combined effect of the azimuthal-to-radial velocity ratio of the two inlet streams ($CH_4$ and $O_2$). The peak yield is achieved with both streams co-rotating at high azimuthal-to-radial velocity ratio of 3, indicating the high azimuthal-to-radial velocity ratio is favorable in creating a wide recirculation region and fast mixing.

Example 3

Figure 13:
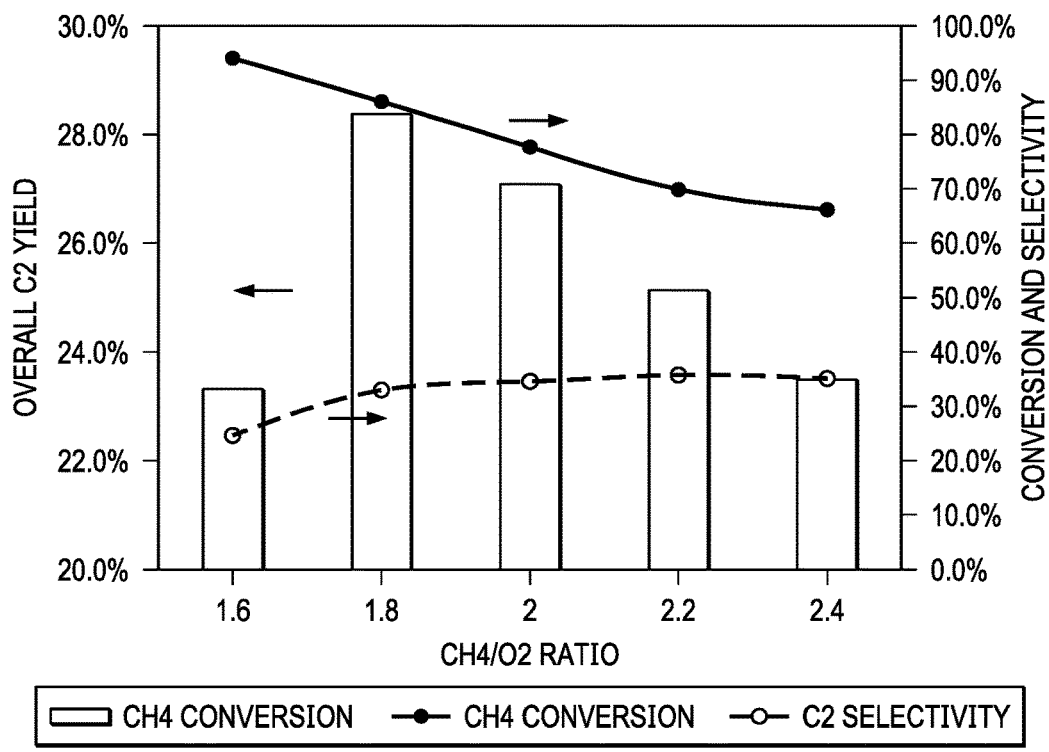
FIG. 13 is a plot of the effect of the methane/$O_2$ molar feed ratios on pyrolysis performance in a lab scale pyrolysis reactor unit model of Example 3.

FIG. 13 shows the effect of methane/oxygen mole ratio on the pyrolysis performance, varying the ratio from 1.6 to 2.4. The sensitivity analysis shows that the overall methane conversion decreases along with the increasing methane/oxygen ratio, due to the combustion temperature and available thermal heat for pyrolysis. On the other hand, the selectivity is slightly increased from a ratio of 1.6 to a ratio of around 2. As a product of these two metrics, the overall $C_2$+ yield finds a peak at ratio around 1.8 at this specific scale reaches around 28.2% under certain operating conditions. It is noteworthy that the optimized methane/oxygen ratio may vary under different reactor scale, heat loss, as well as operating pressures.

Example 4

Figure 14:
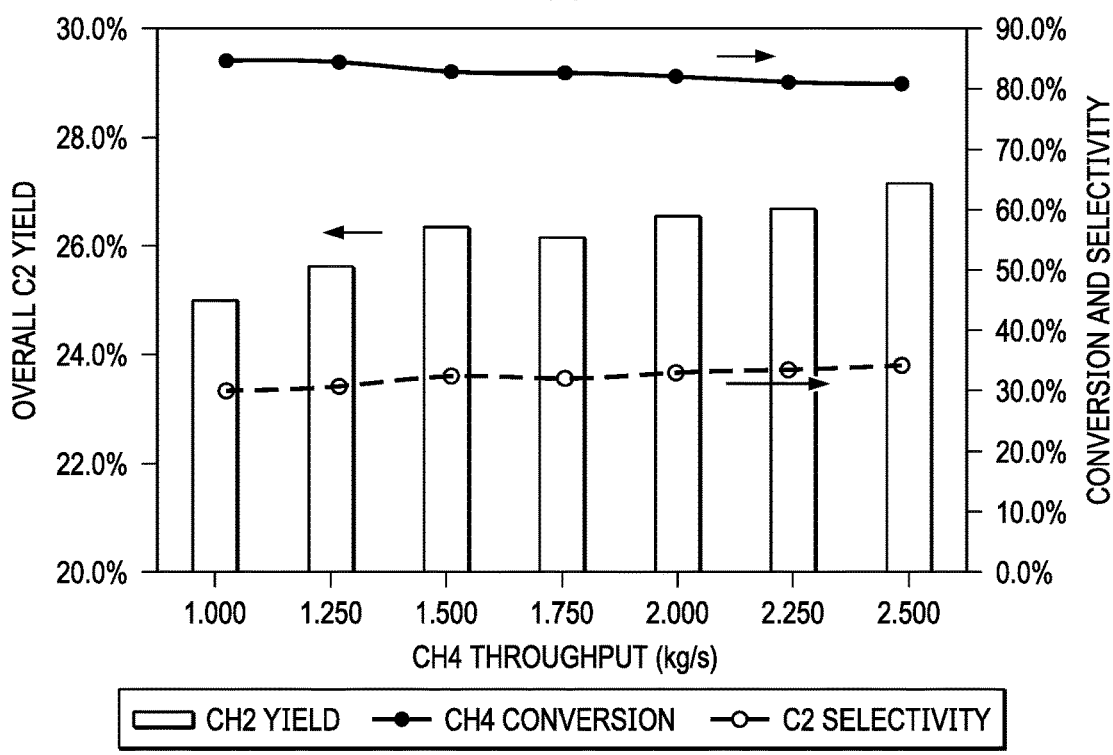
FIG. 14 is a plot of the numerical simulation results summarized as the mass flow rate increases for both $CH_4$ and $O_2$ while maintaining the methane/oxygen feeding ratio of Example 4.
Figure 15:
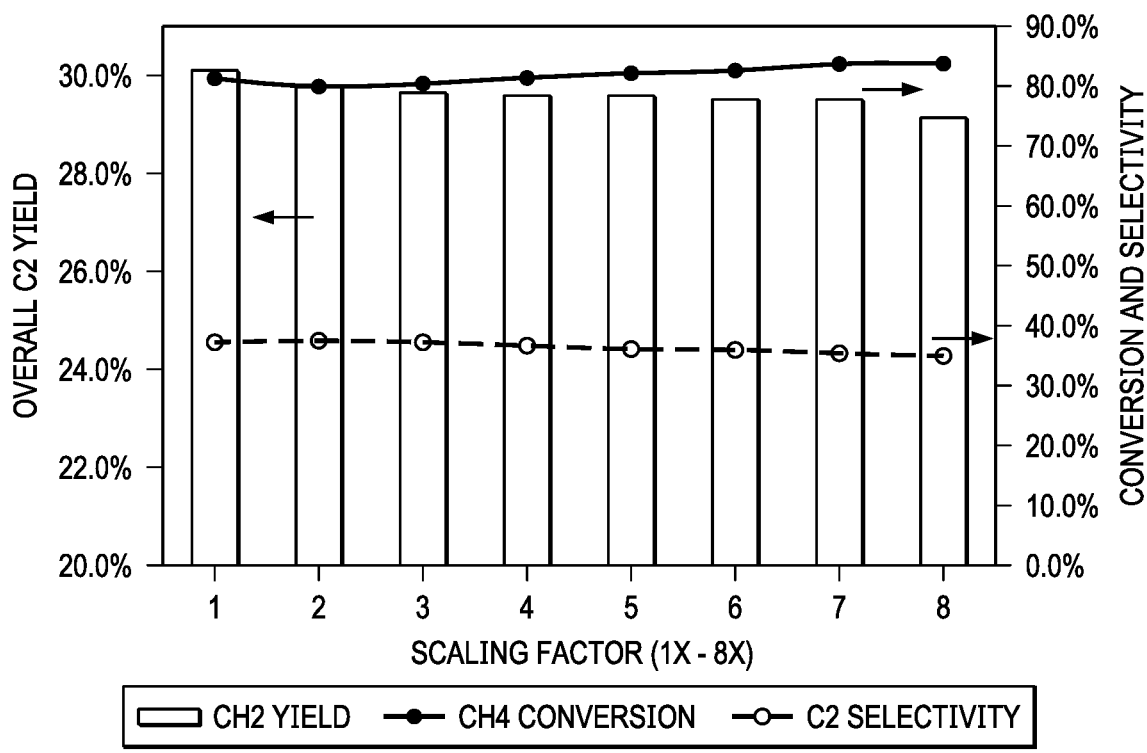
FIG. 15 is a plot of the numerical simulation results as all dimensions of the reactor described herein are uniformly scaled-up, while the flow velocity is maintained in all cases, for Example 4.

Referring to FIG. 14, the numerical simulation results are summarized as the mass flow rate increases for both $CH_4$ and $O_2$ while maintaining the methane/oxygen feeding ratio. The $C_2$+ yield slightly increases with the throughput because of the enhanced mixing effect under increasing Re number. Shorter residence time may also be favorable for higher $C_2$+ yield if high conversion is not sacrificed. FIG. 15 summarizes the numerical simulation results as all dimensions of the reactor described herein are uniformly scaled-up, while the flow velocity is maintained in all cases. Results show that $CH_4$ conversion, $C_2$+ yield, and $C_2$+ selectivity remain nearly invariant in this dimension range.

While the invention has been shown in some of its forms, it should be apparent to those skilled in the art that it is not so limited, but is susceptible to various changes and modifications without departing from the scope of the invention based on experimental data or other optimizations considering the overall economics of the process. Accordingly, it is appropriate that the appended claims be construed broadly and in a manner consistent with the scope of the invention.

We claim:

1. A method of converting light alkanes to pyrolysis products, the method comprising:
providing a pyrolysis reactor comprising:
a pyrolysis reactor vessel having a reactor wall that defines a pyrolysis reaction chamber;
a burner assembly having a burner conduit with a circumferential wall that surrounds a central longitudinal axis and extends from opposite upstream and downstream ends of the burner conduit, the circumferential wall having an annular constricted neck portion located between the downstream and upstream ends of the burner conduit, the downstream end of the burner conduit being in fluid communication with the reaction chamber of the pyrolysis reactor, the upstream end of the burner conduit forming a burner assembly inlet; and
a pyrolysis feed assembly having an annular alkane gas flow space and an annular oxygen gas flow space that discharge into a central mixing chamber that is in fluid communication with the burner assembly inlet;
introducing an alkane-containing gas feed stream of a pyrolysis feed into the annular alkane gas flow space and an oxygen-containing gas feed stream of the pyrolysis feed into the annular oxygen gas flow space so that the alkane-containing gas feed stream and the oxygen-containing gas feed stream pass through said flow spaces perpendicularly to the central longitudinal axis of the burner conduit in an inwardly spiraling fluid flow pattern within said flow spaces that flows about the central longitudinal axis of the burner conduit, with the oxygen-containing gas feed stream from the oxygen gas flow space and alkane-containing gas feed stream from the alkane gas flow space being discharged into the mixing chamber so that the alkane-containing gas and oxygen-containing gas feed streams are mixed together and form a swirling gas mixture within the mixing chamber;
allowing the swirling gas mixture to pass through the burner conduit, with at least a portion of the swirling gas mixture forming a thin, annular mixed gas flow layer immediately adjacent to the burner conduit, and wherein a portion of the swirling gas mixture is combusted as the swirling gas mixture passes through the burner conduit to provide conditions suitable for pyrolysis of the alkane gas from the alkane-containing gas feed stream within the pyrolysis reaction chamber of the reactor vessel, with a portion of the alkane gas being converted to pyrolysis products within the pyrolysis reaction chamber; and
removing pyrolysis products from the reaction chamber of the reactor vessel; and
wherein gas flow through the pyrolysis reactor is at subsonic flow velocities.

2. The method of claim 1, wherein:
a back flow of flue gases is formed within the pyrolysis reactor that flows upstream and radially inward from the thin, annular mixed gas flow layer along the central longitudinal axis toward the upstream end of the burner conduit.

3. The method of claim 1, wherein:
the alkane gas of the alkane-containing gas feed stream is a methane gas or natural gas.

4. The method of claim 3, wherein:
the methane gas or natural gas (NG) of the alkane-containing gas feed stream and oxygen of the oxygen-containing gas feed stream are introduced into the pyrolysis feed assembly in a $CH_4/O_2$ or $NG/O_2$ molar ratio of from 1 to 5.

5. The method of claim 1, wherein:
pyrolysis products are removed from the reaction chamber and are quenched within a quenching unit.

6. The method of claim 1, wherein:
the azimuthal-to-radial velocity ratio of each of the alkane-containing gas feed stream and the oxygen-containing gas feed stream within the annular flow spaces is from 0 to 30.

7. The method of claim 1, wherein:
alkane-containing gas feed stream and the oxygen-containing gas feed stream are each introduced into the respective annular flow spaces in the same rotational direction.

8. The method of claim 1, wherein:
at least one of the annular alkane gas and oxygen gas flow spaces is provided with circumferentially spaced apart guide vanes oriented to facilitate forming the inwardly spiraling fluid flow pattern within said at least one flow spaces.

9. The method of claim 8, wherein:
the guide vanes are movable to selected positions to provided selected azimuthal-to-radial velocity ratios of each of the alkane-containing gas feed stream and the oxygen-containing gas feed stream within the annular flow spaces.

10. The method of claim 1, wherein:
gas flow through the pyrolysis reactor is at flow velocities of from 500 m/s or less.

11. The method of claim 1, wherein:
the circumferential wall of the burner conduit from the downstream end to the annular constricted neck portion, and optionally an upstream portion of the reactor wall of the pyrolysis reaction chamber that joins the circumferential wall of the burner conduit, is configured as a smooth, continuous wall that follows contour lines of an ellipsoidal cap or spherical cap shape.

12. The method of claim 1, wherein:
the interior of the reactor wall is a refractory material.

13. The method of claim 1, wherein:
the annular alkane gas flow space and the annular oxygen gas flow space are defined by planar walls of the pyrolysis feed assembly that are oriented perpendicular to the central longitudinal axis of the burner conduit.

14. The method of claim 1, wherein:
the annular alkane gas flow space is located at a position along the central longitudinal axis downstream from the annular oxygen gas flow space.

\* \* \* \* \*